(12) United States Patent
Sheahan (10) Patent No.: US 9,573,282 B1
(45) Date of Patent: Feb. 21, 2017

(54) KNIFE WITH PUSH BUTTON ASSISTED-OPEN MECHANISM

(71) Applicant: Neptune Trading Inc., Ontario, CA (US)

(72) Inventor: Graeme Sheahan, Kew (AU)

(73) Assignee: Neptune Trading Inc., Ontario, CA (US)

(*) Notice: Subject to any disclaimer, the term of this patent is extended or adjusted under 35 U.S.C. 154(b) by 0 days.

(21) Appl. No.: 15/165,859

(22) Filed: May 26, 2016

(51) Int. Cl.
| | |
|---|---|
| B26B 1/04 | (2006.01) |
| B25B 15/00 | (2006.01) |
| A47G 21/02 | (2006.01) |
| A47G 21/04 | (2006.01) |
| B67B 7/04 | (2006.01) |
| B67B 7/16 | (2006.01) |
| B67B 7/46 | (2006.01) |
| B25G 3/38 | (2006.01) |
| A61C 15/02 | (2006.01) |
| A61C 15/04 | (2006.01) |

(52) U.S. Cl.
CPC .............. B26B 1/048 (2013.01); A47G 21/023 (2013.01); A47G 21/04 (2013.01); A61C 15/02 (2013.01); A61C 15/046 (2013.01); B25B 15/00 (2013.01); B25G 3/38 (2013.01); B67B 7/04 (2013.01); B67B 7/16 (2013.01); B67B 7/30 (2013.01); B67B 2007/303 (2013.01)

(58) Field of Classification Search
CPC ...... A47G 21/023; A47G 21/04; A61C 15/02; A61C 15/046; B25B 15/00; B67B 7/04; B67B 7/16; B67B 7/30; B67B 2007/303; B26B 1/04; B26B 1/048; B25G 3/38

USPC .......................................... 30/150–162; 7/118
See application file for complete search history.

(56) References Cited

U.S. PATENT DOCUMENTS

| | | | |
|---|---|---|---|
| 533,219 | A | 1/1895 | Hardy |
| 616,689 | A | 12/1898 | Ruettgers |
| 1,234,345 | A | 7/1917 | Keeran |
| 5,896,665 | A | 4/1999 | Harris |
| 7,062,856 | B2 | 6/2006 | Moser |
| 7,080,457 | B2 | 7/2006 | Sullivan |
| 7,380,340 | B1 | 6/2008 | Lerch |
| 8,020,302 | B2 | 9/2011 | Kao |
| 8,438,738 | B2 * | 5/2013 | Lo ............ B26B 1/044 30/155 |
| 8,511,208 | B1 | 8/2013 | Frazer |
| 8,939,053 | B2 | 1/2015 | Pardue |
| 9,132,558 | B2 | 9/2015 | Millhouse |

(Continued)

*Primary Examiner* — Ghassem Alie
*Assistant Examiner* — Nhat Chieu Do
(74) *Attorney, Agent, or Firm* — Levine Bagade Han LLP (57) ABSTRACT

A folding knife with a push button assisted-open mechanism is disclosed. The folding knife comprising a handle with at least two handle sides spaced apart and defining a blade cavity; a blade pivotally connected to the handle, wherein the blade comprises a drive pin connected to and extending out from a side of the blade; a toggle component pivotally connected to at least one of the at least two handle sides at a pivot pin, wherein the toggle component comprises a retaining notch; and a spring comprising an arcuate segment along a longitudinal axis of the spring. The spring is coupled to at least one of the at least two handle sides at one end and the toggle component at another end, wherein the drive pin is positioned within the retaining notch when at least part of the blade is folded into the blade cavity.

9 Claims, 7 Drawing Sheets

(56) References Cited

U.S. PATENT DOCUMENTS 9,138,903 B2 9/2015 Vellekamp
2009/0119926 A1* 5/2009 Nenadic ................... B26B 1/04
30/161

* cited by examiner

FIGURE 6

KNIFE WITH PUSH BUTTON ASSISTED-OPEN MECHANISM

FIELD OF TECHNOLOGY

The present disclosure relates generally to the field of folding knives, and, more specifically, to a folding knife with a push button assisted-open mechanism.

BACKGROUND

Folding knives with assisted-open mechanisms are widely used by hunters, carpenters, and outdoor enthusiasts for their portability and safe handling when folded. Traditional assisted-open folding knives typically contain a knife blade having a protrusion such as a stud, pin, or oversized tang extending out from an exposed portion of the knife blade when the folding knife is in a closed position. When deploying such knives, a user typically pushes on the protrusion to actuate the knife blade.

However, such traditional assisted-open folding knives are often difficult to maneuver and may harm the user's fingers or hands when the user is unfamiliar with the operation of the assisted-open mechanism. For example, some assisted-open folding knives may require the user to place the user's thumb dangerously close to the blade of the knife in order to actuate the knife blade. In addition, the knife blade of such assisted-open folding knives can be difficult to deploy and may require the user to hold the handle of the knife with one hand and pull on the knife blade with the user's other hand in order to fully deploy the knife blade. In other cases, some assisted-open folding knives may be deployed on accident when a part of the user's body or an object brushes against the protrusion on the knife blade.

Therefore, a solution is needed which allows the user to easily and safely actuate the knife blade of an assisted-open folding knife with one hand. Such a solution should be intuitive to understand for novice users and should provide features that prevent the knife blade from inadvertently actuating when the folding knife is in a user's pocket or otherwise being carried in transit.

SUMMARY

A folding knife with a push button assisted-open mechanism is disclosed. In one embodiment, the folding knife can include a handle having at least two handle sides spaced apart. The two handle sides can define a blade cavity in between the two handle sides. A blade can be pivotally connected to the handle. The blade can have a drive pin connected to and extending out from a side of the blade. A toggle component can be pivotally connected to at least one of the two handle sides at a pivot pin. The toggle component can have a retaining notch defined along an edge of the toggle component. The folding knife can include a spring having an arcuate segment or a bended segment along a longitudinal axis of the spring.

The spring can be coupled to at least one of the two handle sides at one end and the toggle component at the other end. The spring can be a tension spring comprising at least one coiled segment, the arcuate segment, and one or more straight segments. The drive pin of the blade can be positioned within the retaining notch when at least part of the blade is folded into the blade cavity.

The folding knife can also include a clearance slot defined along at least one of the two handle sides and part of the drive pin can project through the clearance slot. The toggle component can also include a button top. The toggle component can rotate in a toggle rotational direction (e.g., a counterclockwise direction) in response to a force applied to the button top by a user of the folding knife in the direction of the handle bottom. The blade can be deployed out of the blade cavity in a blade rotational direction (e.g., a clockwise direction) in response to the rotation of the toggle component. The toggle rotational direction can be counter to the blade rotational direction. The drive pin can move within the clearance slot as the blade is rotated. The retaining notch can be defined in part by a toggle nose of the toggle component and the blade can be deployed when the toggle nose actuates or biases the drive pin of the blade when the toggle component is rotated in the toggle rotational direction.

The spring can pull the toggle component in a first rotational direction (e.g., a clockwise direction) when the folding knife is in a folded configuration. The spring can also pull the toggle component in a second rotational direction (e.g., a counterclockwise direction) when the folding knife is in an open configuration. In these embodiments, the first rotational direction can be counter to the second rotational direction. The spring can pull the toggle component in the second rotational direction when the toggle component passes an over-center position in response to a force applied to the button top by a user of the folding knife in the direction of the handle bottom. The arcuate segment of the spring can partially surround or encompass the pivot pin when the spring pulls the toggle component in the first rotational direction.

The handle can further include at least one outer handle side and at least two inner handle sides. The toggle component can be positioned in between the at least one outer handle side and one of the inner handle sides.

The blade of the folding knife can also include a partial tang and the partial tang can rotate in between the at least two inner handle sides without protruding from a handle top of the handle.

The folding knife can further include a locking slide bar coupled to a locking slide pin. The locking slide pin can prevent the toggle component from rotating when the locking slide pin contacts and pushes against a locking notch defined along an edge of the toggle component.

Also disclosed is an embodiment of a folding utility tool. The folding utility tool can include a handle having at least two handle sides spaced apart. The two handle sides can define a tool cavity in between the two handle sides. A tool arm can be pivotally connected to the handle. The tool arm can have a drive pin connected to and extending out from a side of the tool arm. A toggle component can be pivotally connected to at least one of the two handle sides at a pivot pin. The toggle component can have a retaining notch defined along an edge of the toggle component. The folding utility tool can include a spring having an arcuate or arc-like segment or a bended segment along a longitudinal axis of the spring.

The spring can be coupled to at least one of the two handle sides at one end and the toggle component at the other end. The spring can be a tension spring comprising at least one coiled segment, the arcuate segment, and one or more straight segments. The drive pin of the tool arm can be positioned within the retaining notch when at least part of the tool arm is folded into the tool cavity.

The folding utility tool can also include a clearance slot defined along at least one of the two handle sides and part of the drive pin can project through the clearance slot. The toggle component can also include a button top. The toggle component can rotate in a toggle rotational direction (e.g., a counterclockwise direction) in response to a force applied to the button top by a user of the folding utility tool in the direction of the handle bottom. The tool arm can be deployed out of the tool cavity in an arm rotational direction (e.g., a clockwise direction) in response to the rotation of the toggle component. The toggle rotational direction can be counter to the arm rotational direction. The drive pin can move within the clearance slot as the tool arm is rotated. The retaining notch can be defined in part by a toggle nose of the toggle component and the tool arm can be deployed when the toggle nose actuates or biases the drive pin of the tool arm when the toggle component is rotated in the toggle rotational direction.

The spring can pull the toggle component in a first rotational direction (e.g., a clockwise direction) when the folding utility tool is in a folded configuration. The spring can also pull the toggle component in a second rotational direction (e.g., a counterclockwise direction) when the folding utility tool is in an open configuration. In these embodiments, the first rotational direction can be counter to the second rotational direction. The spring can pull the toggle component in the second rotational direction when the toggle component passes an over-center position in response to a force applied to the button top by a user of the folding utility tool in the direction of the handle bottom. The arcuate segment of the spring can partially surround or encompass the pivot pin when the spring pulls the toggle component in the first rotational direction.

The handle can further include at least one outer handle side and at least two inner handle sides. The toggle component can be positioned in between the at least one outer handle side and one of the inner handle sides.

The folding utility tool can include a tool head coupled to the tool arm. The tool head can include a part of a screwdriver, a fork, a spoon, a toothpick, a flossing tool, a corkscrew, a bottle opener, or a can opener. The tool head can be folded into the tool cavity when the folding utility tool is in the folded configuration.

The folding utility tool can further include a locking slide bar coupled to a locking slide pin. The locking slide pin can prevent the toggle component from rotating when the locking slide pin contacts and pushes against a locking notch defined along an edge of the toggle component.

DETAILED DESCRIPTION

Figure 1:
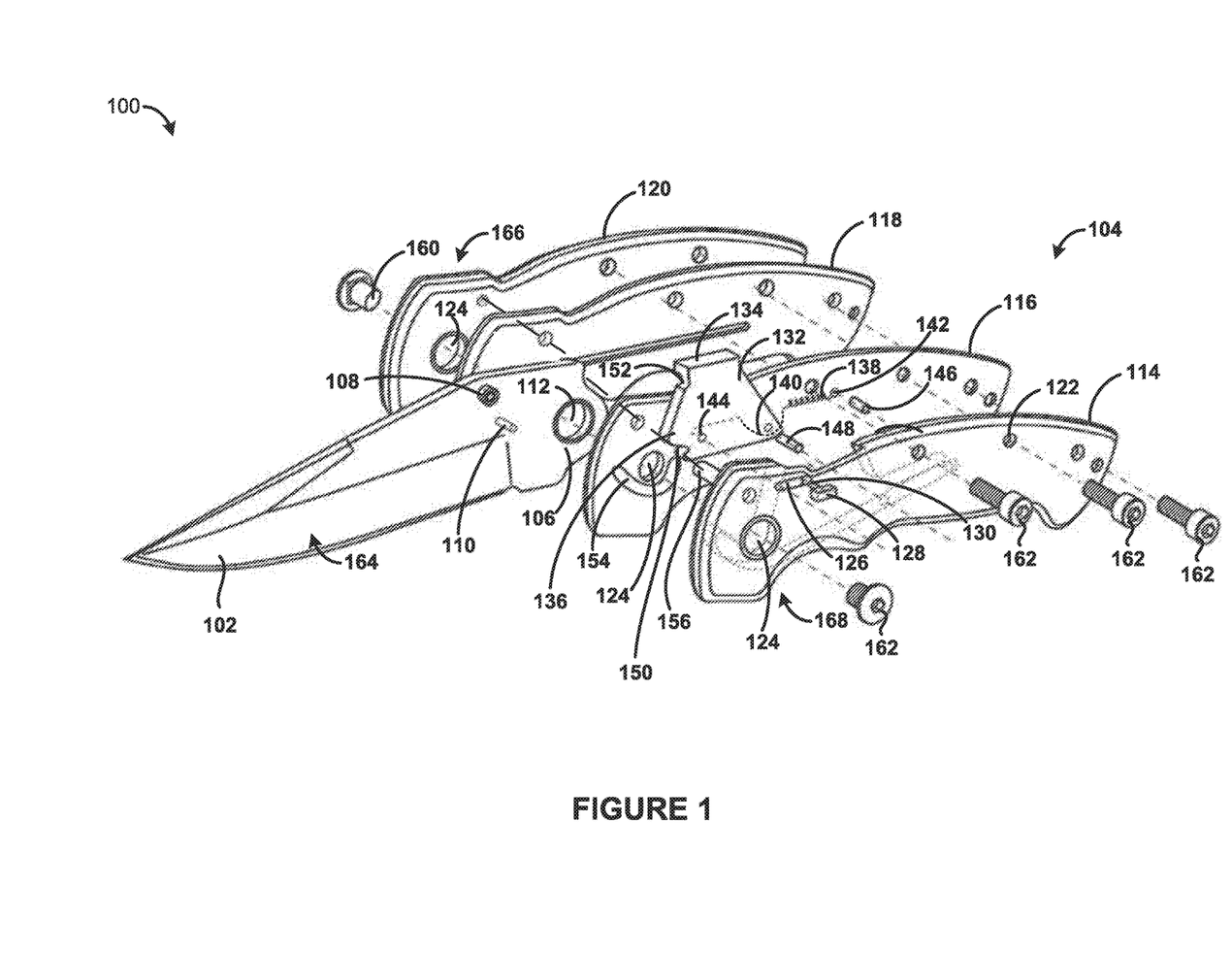
FIG. 1 illustrates an exploded perspective view of an embodiment of a folding knife with a push button assisted-open mechanism.

FIG. 1 illustrates an exploded perspective view of a folding knife 100 with a push button assisted-open mechanism in one or more embodiments. In one embodiment, the folding knife 100 can include a handle 104 having a first outer handle side 114, a first inner handle side 116, a second inner handle side 118, and a second outer handle side 120. In other embodiments, the folding knife 100 can include additional handle sides or handle adornments in between the aforementioned handle sides or attached to such handle sides. The handle 104 can include a handle top 166 and a handle bottom 168.

The handle bottom 168 can be a portion of the handle 104 configured to receive the fingers of a user when the user grips the handle 104 in a handshake grip. For example, the handle bottom 168 can be defined by one or more handle grooves, finger holds, or grips along an edge of the handle bottom 168. The handle top 166 can be a portion of the handle 104 configured to receive the palm of the user when the user grips the handle 104 in the handshake grip. The handle top 166 can be defined by one or more divots, dips, or cutouts allowing a user to access a component of the folding knife 100 in between the handle sides. The handle 104 can also include a base end and a blade end opposite the base end.

The handle 104 including the first outer handle side 114, the first inner handle side 116, the second inner handle side 118, and the second outer handle side 120 can have a plurality of handle bores 122 or bore holes along a length of the handle 104 in between the base end and the blade end. The first outer handle side 114, the first inner handle side 116, the second inner handle side 118, and the second outer handle side 120 can each have the same handle bores 122 aligned laterally so a fastener 162 or pin threads through the laterally aligned handle bores 122 to attach or couple the first outer handle side 114 to the first inner handle side 116, the first inner handle side 116 to the second inner handle side 118, and the second inner handle side 118 to the second outer handle side 120.

Each of the first outer handle side 114, the first inner handle side 116, the second inner handle side 118, and the second outer handle side 120 can be shaped similar to one another and can serve as one piece or layer of the handle 104. For example, the first outer handle side 114 and the second outer handle side 120 can serve as the outer covering of the handle 104 and the first inner handle side 116 and the second inner handle side 118 can serve as the inner layers of the handle 104.

The handle 104 can be fabricated from or comprise a polymer, a metal, wood or other organic material, a ceramic, or a composite thereof. For example, the handle 104 can be fabricated from or comprise acrylonitrile butadiene styrene (ABS) plastic, polycarbonate, polypropylene, rubber, or a combination thereof. Also, for example, the handle 104 can be fabricated from or comprise stainless steel, titanium, an alloy thereof, or any combination therewith.

The first inner handle side 116 can be coupled to the second inner handle side 118 by a plurality of fasteners 162 or pins and can define a blade cavity 300 (see FIG. 3) in between the first inner handle side 116 and the second inner handle side 118. The fasteners 162 can include screws, bolts, nuts, washers, pins, flanges, spacers, or a combination thereof.

The handle bores 122 can comprise a plurality of handle axle bores 124. The folding knife 100 can comprise a blade 102 pivotally connected to the handle 104 at the plurality of handle axle bores 124. The blade 102 can have a blade axle bore 112 and the blade 102 can pivot or rotate around a blade axle 160 thread through the handle axle bores 124 and the blade axle bore 112. In some embodiments, the blade axle 160 can be a rod or pin serving as part of a fastener 162.

The blade 102 can have a drive pin 110 connected to and extending or projecting out from a surface of the blade 102. The blade surface having the drive pin 110 can be referred to as the pin side 164 of the blade 102. In one embodiment, the drive pin 110 can extend or project out orthogonally from the pin side 164 of the blade 102. In some embodiments, the pin side 164 of the blade 102 can also have a thumb stud 108 connected to and extending or projecting out from the blade surface. In one embodiment, the thumb stud 108 can be positioned above the drive pin 110 or proximal to the handle top 166 relative to the drive pin 110. In other embodiments not shown in the figures, the thumb stud 108 can be positioned below the drive pin 110 or proximal to the handle bottom 168 relative to the drive pin 110.

The blade 102 can be fabricated from or comprise a metal, a polymer, or a composite thereof. For example, the blade 102 can be fabricated from or comprise stainless steel. In other embodiments, the blade 102 can be fabricated from or comprise carbon steel, cobalt, titanium, ceramics, or alloys thereof. In additional embodiments, the blade 102 can be fabricated from or comprise a polymer such as ABS plastic, polycarbonate, or a combination thereof.

In one embodiment, the folding knife 100 can have a clearance slot 154 defined along the first inner handle side 116. In other embodiments, the folding knife 100 can have multiple clearance slots 154 defined along the first inner handle side 116, the first outer handle side 114, the second inner handle side 118, the second outer handle side 120, or a combination thereof. In these embodiments, the multiple clearance slots 154 can be laterally aligned.

The clearance slot 154 can be an arcuate or substantially arch-shaped clearance slot as shown in FIGS. 1, 2A, 2B, 2C, 2D, and 4. In other embodiments, the clearance slot 154 can be an opening shaped as a circle or half-circle.

At least a portion of the drive pin 110 can be located within the clearance slot 154 while other portions of the drive pin 110 can project or extend through the clearance slot 154 as the blade 102 pivotally rotates around the blade axle 160.

The folding knife 100 can include a toggle component 132 pivotally connected to the handle 104 at a pivot pin 148. In one embodiment, the toggle component 132 can be pivotally connected to the first inner handle side 116, the first outer handle side 114, or a combination thereof.

The toggle component 132 can have a button top 134, a toggle nose 136, or a combination thereof. The toggle component 132 also can have a retaining notch 150 and a locking notch 152 defined along an edge of the toggle component 132. In one embodiment, the retaining notch 150 and the locking notch 152 can be defined along the same edge of the toggle component 132. In some embodiments, the toggle component 132 can be substantially shaped as a trapezoid. For example, the toggle component 132 can be shaped as an acute or obtuse trapezoid having a thickness between 1.0 mm and 5.0 mm. In other embodiments, the toggle component 132 can be shaped as a triangle, a rectangle, a rhombus or diamond, or a parallelogram.

The button top 134 can be a portion of the toggle component 132 projecting out from the handle top 166. The button top 134 can be a portion of the toggle component 132 perpendicular to the substantially trapezoidal body of the toggle component 132. For example, the button top 134 can jut out from the trapezoidal body of the toggle component 132 and act as an overhang covering or obscuring a portion of the handle top 166. In another embodiment, the button top 134 can be flush with the handle top 166 when the folding knife 100 is in a folded configuration 200 (see FIG. 2A).

A user of the folding knife 100 can press on the button top 134 to actuate and deploy the blade 102. The button top 134 can translate a force applied to the button top 134 in the direction of the handle bottom 166 to the rest of the toggle component 132 and the force can rotate the toggle component 132 in a rotational direction such as a counterclockwise direction when viewed from the first outer handle side 114 to the second outer handle side 120.

The toggle component 132 can be pivotally connected to the handle 104 at or near a vertex or corner of the toggle component 132. When the toggle component 132 is substantially shaped as a trapezoid, the toggle component 132 can be pivotally connected to the handle 104 at an acute vertex or corner of the base of the trapezoid. In this embodiment, the retaining notch 150 of the toggle component 132 can be defined at the other acute vertex or corner of the base of the trapezoid.

The retaining notch 150 can be defined by the toggle nose 136 and the base edge of the toggle component 132. The toggle nose 136 can extend or protrude out past the retaining notch 150. In other embodiments, the retaining notch 150 can be a groove or divot defined along a side edge of the toggle component 132.

The drive pin 110 can be positioned within the retaining notch 150 when the blade 102 is folded into the blade cavity 300 and the folding knife 100 is in the folded configuration 200. The blade 102 can be deployed out of the blade cavity 300 in response to the rotation of the toggle component 132. The toggle nose 136 can actuate the drive pin 110 of the blade 102 by pushing on the portion of the drive pin 110 projecting through the clearance slot 154. The toggle nose 136 can push the drive pin 110 further into the clearance slot 154. The trajectory of the drive pin 110 can follow the shape of the clearance slot 154 as the toggle nose 136 pushes the drive pin 110 toward the blade end of the handle 104.

The blade 102 can be deployed when the movement of the drive pin 110 rotates the blade 102 in a rotational direction counter to the rotation of the toggle component 132. For example, the toggle component 132 can rotate in a counterclockwise direction which, in turn, causes the blade 102 to rotate out of the blade cavity 300 in a clockwise direction. The rotation of the toggle component 132 will be discussed in more detail in the following sections.

In one embodiment, the toggle component 132 can be positioned in between the first outer handle side 114 and the first inner handle side 116. In this embodiment, the clearance slot 154 can be defined along the surface of the first inner handle side 116 and the drive pin can project orthogonally out of the blade surface toward the first outer handle side 114.

In other embodiments not shown in the figures, the toggle component 132 can be positioned in between the second outer handle side 120 and the second inner handle side 118. In these embodiments, the clearance slot 154 can be defined along the surface of the second inner handle side 118 and the drive pin 110 can project orthogonally out of the other blade surface toward the second outer handle side 120. These embodiments allow the folding knife 100 to be used or operated by left-handed or ambidextrous users.

As seen in FIG. 1, the blade 102 can comprise a tang 106. The tang 106 can be a partial tang such as a half or quarter tang. The partial tang can rotate in between the first inner handle side 116 and the second inner handle side 118 without the tang 106 projecting from the handle top 166. In addition, the tang 106 of the blade 102 can be obscured or covered by the handle 104 including the first outer handle side 114 and the second outer handle side 120 when the folding knife 100 is in either the folded configuration 200 or an open configuration 204 (see FIG. 2D). The blade 102 can rotate until a part of the blade 102 makes contact with a stop pin 156.

Although not shown in the figures, it is contemplated by this disclosure that the folding knife 100 can comprise a liner lock coupled to the first inner handle side 116 or the second inner handle side 118. The liner lock can spring out laterally from the inner handle side when the blade 102 is at least partially deployed from the blade cavity 300 and a tip or end of the liner lock can contact or jam against the tang 106 of the blade 102 to lock the blade 102 into place when the folding knife 100 is in the open configuration 204.

The folding knife 100 can also comprise a spring 138 having an arcuate segment 140 or portion along a longitudinal axis 508 (see FIG. 5) of the spring 138. The spring 138 can be fabricated from or comprise a metal, a polymer, or a composite thereof. For example, the spring 138 can be fabricated from or comprise stainless steel. In other embodiments, the spring 138 can be fabricated from or comprise a shape memory material such as Nitinol. In additional embodiments, the spring 138 can be fabricated from or comprise a polymer.

The spring 138 can be coupled to at least one of the first inner handle side 116 and the first outer handle side 114 at one end of the spring 138. The spring 138 can be coupled to at least one of the first inner handle side 116 and the first outer handle side 114 at a first inner handle site 142 by one or more securement pins 146. The spring 138 can also be coupled to the toggle component 132 at the other end of the spring 138 at a toggle site 144 by one or more securement pins 146.

The spring 138 can have one or more coiled segments 400 (see FIG. 4), one or more straight segments, and the arcuate segment 140. The spring 138 can be a tension spring. The arcuate segment 140 of the spring 138 can partially surround the pivot pin 148 about which the toggle component 132 rotates. The arcuate segment 140 can partially surround the pivot pin 148 when the folding knife 100 is in the folded configuration 200.

The folding knife 100 can also comprise a locking mechanism. The locking mechanism can include a locking slide bar 128 having a locking slide pin 130 projecting out from a surface of the locking bar 128. The locking slide pin 130 can lock the toggle component 132 by preventing the toggle component 132 from rotating when the locking slide pin 130 contacts or is partially encompassed by the locking notch 152 of the toggle component 132. The locking slide bar 128, the locking slide pin 130, or a portion therein can be positioned within a lock opening 126 and can slide longitudinally within the lock opening 126. The locking slide pin 130 can extend out orthogonally from an inner surface of the locking slide bar 128 and project through the lock opening 126 to contact the locking notch of the toggle component 132. A user can push the locking slide bar 128 in the direction of the blade end of the handle 104 to disengage the locking mechanism and allow the toggle component 132 to rotate about the pivot pin 148.

Figure 2A:
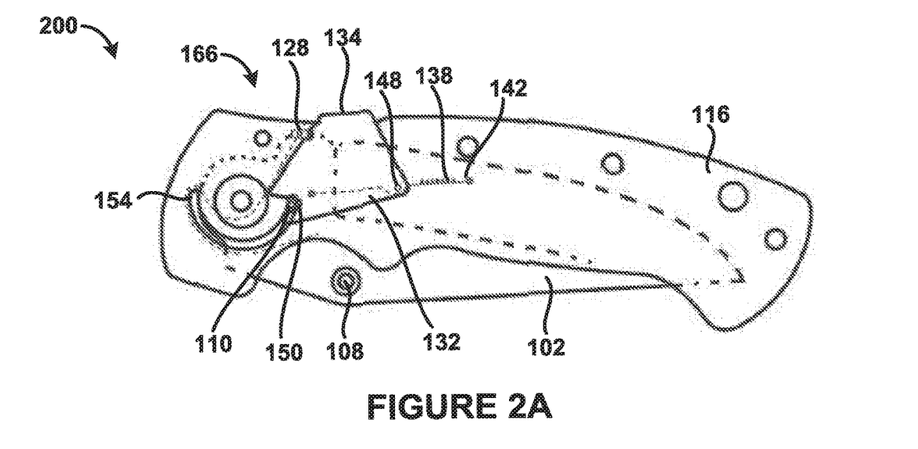
FIG. 2A illustrates a left side view of the folding knife of FIG. 1 assembled and closed into a folded configuration with an outer handle side removed.

FIG. 2A illustrates a left side view of an assembled folding knife 100 in a folded configuration 200. The first outer handle side 114 of the folding knife 100 has been removed in this view to expose the toggle component 132. As shown in FIG. 2A, the drive pin 110 can be within or partially surrounded by the retaining notch 150 of the toggle component 132 when the folding knife 100 is in the folded configuration 200. In addition, a portion of the blade 102, including the blade tip, can be housed in the blade cavity 300 when the folding knife 100 is in the folded configuration 200. In the embodiment shown in FIG. 2A, the thumb stud 108 can be visible when the folding knife 100 is in the folded configuration 200.

Moreover, the locking slide bar 128, the locking slide pin 130, or a combination thereof can lock the toggle component 132 by preventing the toggle component 132 from rotating about the pivot pin 148. The locking slide bar 128, the locking slide pin 130, or a portion therein, can be located within the locking notch 152 when the folding knife 100 is in the folded configuration 200. As will be discussed in more detail in the following sections, the spring 138 can pull the toggle component 132 in a clockwise rotational direction (as viewed in the direction of the second inner handle side 118 from the first inner handle side 116) when the drive pin 110 is housed within the retaining notch 150. Moreover, by pulling the toggle component 132 in the clockwise rotational direction, the button top 134 of the toggle component 132 can protrude past the handle top 166, allowing a user of the folding knife 100 to push on the button top 134 to deploy the blade 102.

FIG. 2A also illustrates that the tang 106 of the blade 102 does not protrude out of or past the handle top 166 when the folding knife 100 is in the folded configuration 200.

Figure 2B:
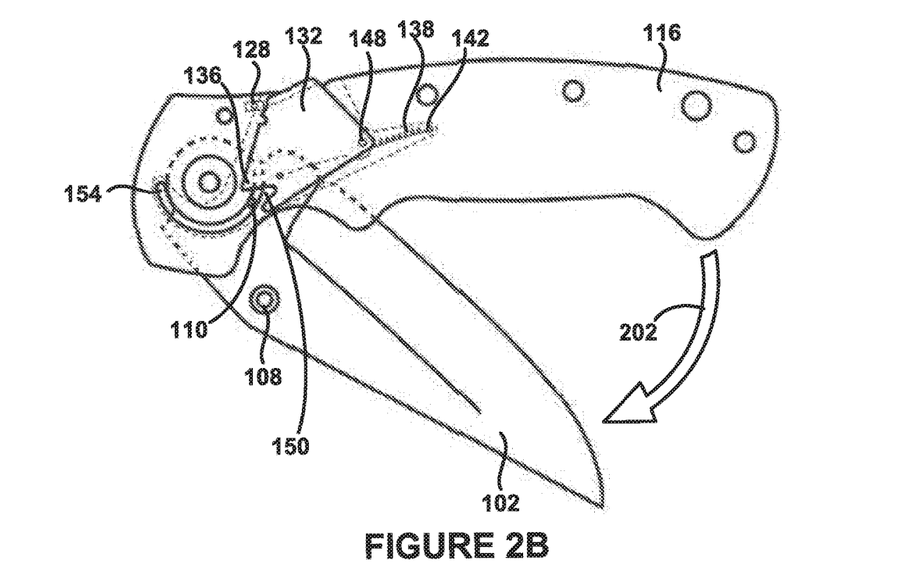
FIG. 2B illustrates the folding knife of FIG. 2A with a blade of the folding knife beginning to deploy.

FIG. 2B illustrates the folding knife 100 of FIG. 2A with the blade 102 beginning to deploy. As shown in FIG. 2B, the blade 102 can be deployed out of the blade cavity 300 in a blade rotational direction 202. The blade rotational direction 202 can be a clockwise direction as viewed in the direction of the second inner handle side 118 from the first inner handle side 116. As shown in FIG. 2B, the drive pin 110 can be forced by the toggle nose 136 out of the retaining notch 150 and along a trajectory following the shape of the clearance slot 154. The blade 102 can be deployed out of the blade cavity 300 in response to a user pressing down on the button top 134 of the toggle component 132. The user can press the button top 134 to cause the toggle component 132 to rotate in a toggle rotational direction 504 (see FIG. 5). The toggle rotational direction 504 can be a counterclockwise direction as viewed in the direction of the second inner handle side 118 from the first inner handle side 116. The toggle rotational direction 504 can be counter to the blade rotational direction 202. Moreover, FIG. 2B shows that the spring 138 can pull the toggle component 132 in a counterclockwise rotational direction (as viewed in the direction of the second inner handle side 118 from the first inner handle side 116).

In the embodiment shown in FIG. 2A, the button top 134 can protrude or extend beyond the handle top 166. In other embodiments not shown in FIG. 2A, the button top 134 can be flush with the handle top 166 and the handle top 166 can be defined by a divot or cut-out portion allowing a user access to the button top 134.

Figure 2C:
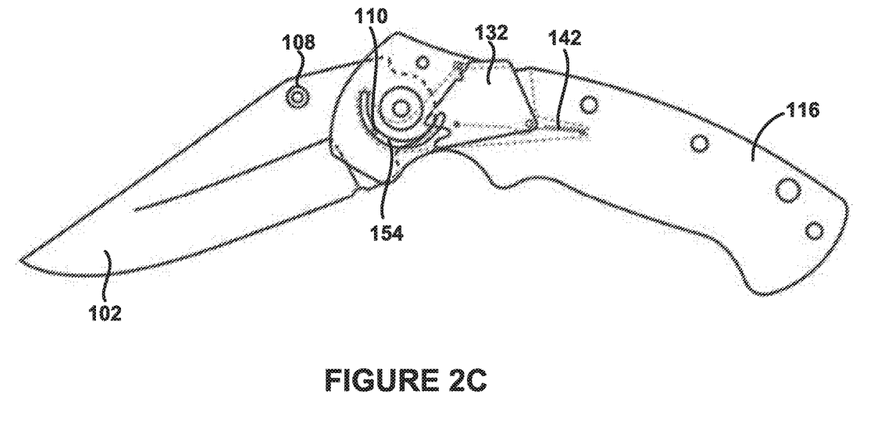
FIG. 2C illustrates the folding knife of FIG. 2A with the blade of the folding knife in mid-deployment.

FIG. 2C illustrates the folding knife 100 of FIG. 2A with the blade 102 of the folding knife 100 in mid-deployment. As shown in FIG. 2C, the drive pin 110 can be positioned further along the curve of the clearance slot 154. The drive pin 110 can be carried further along the curve of the clearance slot 154 by the rotational motion of the blade 102, the force exerted on the drive pin 110 by the toggle nose 136, or a combination thereof. For example, the toggle nose 136 can exert a force on the drive pin 110 as the spring 138 pulls the toggle component 132 in the counterclockwise rotational direction.

The blade 102 of the folding knife 100 can be automatically deployed up to this point in its rotational trajectory in response to the user pushing on the button top 134 of the toggle component 132. At this point, the user can further deploy the blade 102 and guide the folding knife 100 into the open configuration 204 of FIG. 2D by using the thumb stud 108 of the blade 102. The design of the folding knife 100, including the tension of the spring 138 and the shapes of the toggle component 132 and clearance slot 154, can be configured to prevent the blade 102 from being fully deployed in response to the user pressing on the button top 134 of the toggle component 132. This design allows the folding knife 100 to function as an assisted-open knife rather than a switchblade (which is outlawed by certain U.S. and international jurisdictions).

Figure 2D:
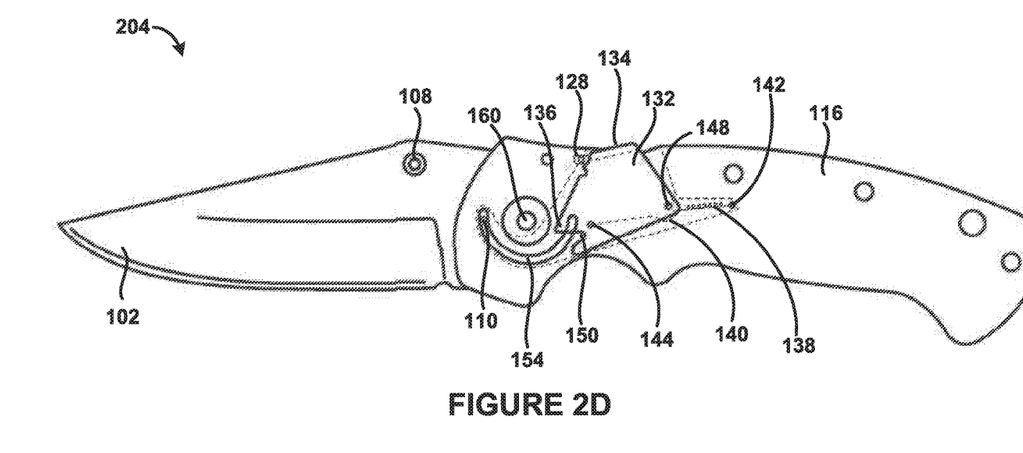
FIG. 2D illustrates the folding knife of FIG. 2A in an open configuration.

FIG. 2D illustrates the folding knife 100 of FIG. 2A in an open configuration 204. As shown in FIG. 2D, the drive pin 110 can be located at an opposite end of the clearance slot 154 from its initial starting point. In the embodiment shown in FIG. 2D, a portion of the button top 134 can be sunk into the handle top 166 when the folding knife 100 is in the open configuration 204. The spring 138 can pull the toggle component 132 in a counterclockwise rotational direction when the folding knife 100 is in the open configuration 204.

FIGS. 2B, 2C, and 2D also show that the tang 106 of the blade 102 can be a partial tang. The partial tang can rotate in between the first inner handle side 116 and the second inner handle side 118 when the blade 102 rotates in the blade rotational direction 202. In one or more embodiments, the partial tang can rotate in between the first inner handle side 116 and the second inner handle side 118 without the partial tang protruding from the handle top 166.

Figure 2E:
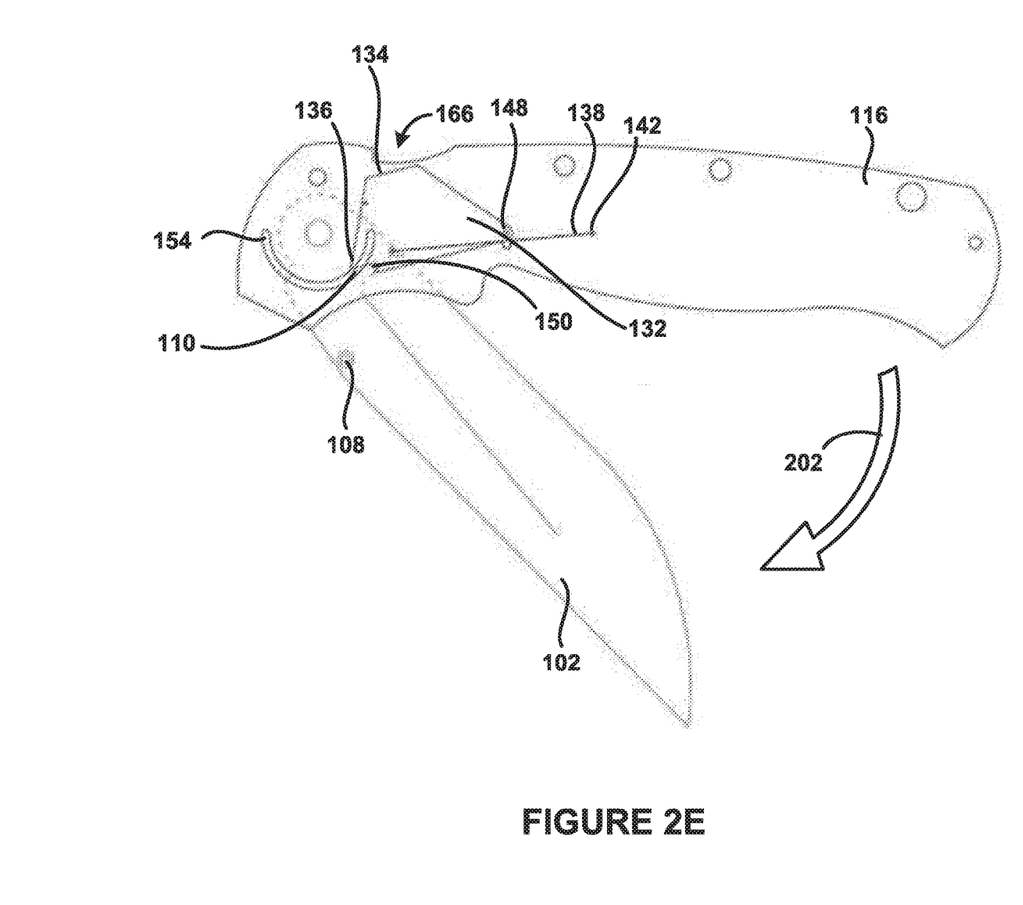
FIG. 2E illustrates another embodiment of the folding knife with a button top of the folding knife obscured by a handle top.

FIG. 2E illustrates another embodiment of the folding knife 100 with the button top 134 of the toggle component 132 below the handle top 166 or obscured by the handle top 166 in response to a user pressing on the button top 134. For example, a user can press on the button top 134 of the toggle component 132 to deploy the blade 102. The button top 134 of the toggle component 132 can be below or obscured by the handle top 166 when the spring pulls the toggle component 132 in a second rotational direction 502 (see FIG. 5). The spring 138 can pull the toggle component 132 in the second rotational direction 502 when the toggle component 132 has passed an over-center position 510 (see FIG. 5). The toggle component 132 can be inaccessible to a user of the folding knife 100 when the button top 134 is below or obscured by the handle top 166.

Once the button top 134 is below the handle top 166, the toggle component 132 can rotate in a first rotational direction 500 (see FIG. 5) to return the toggle component 132 to its original position when the blade 102 is folded back into the blade cavity 300 (See FIG. 3). When the blade is folded back into the blade cavity 300, the drive pin 110 of the blade 102 can push back on the toggle component 132, including the retaining notch 150 of the toggle component 132, the toggle nose 136, or a combination thereof to rotate the toggle component in the first rotational direction 500. The button top 134 can once again be accessible to the user of the folding knife 100 when the toggle component 132 is being pulled by the spring 138 in the first rotational direction 500.

Figure 3:
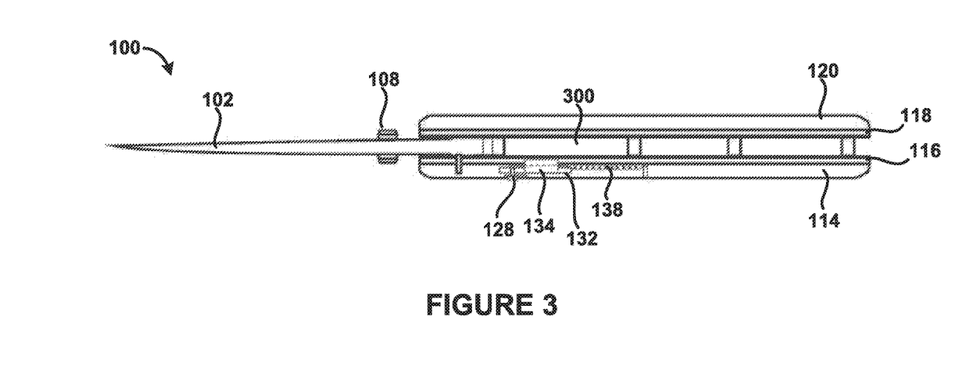
FIG. 3 illustrates a top plan view of the folding knife of FIG. 1 in an assembled state and open configuration.

FIG. 3 illustrates a top plan view of the folding knife 100 of FIG. 1 in an assembled state. FIG. 3 shows that the first inner handle side 116 can be spaced apart from the second inner handle side 118 and define a blade cavity 300 in between the first inner handle side 116 and the second inner handle side 118. Moreover, FIG. 3 shows that the toggle component 132 and the spring 138 can be housed in between the first outer handle side 114 and the first inner handle side 116.

Although not shown in FIG. 3, it is contemplated by this disclosure that the folding knife 100 can comprise a liner lock coupled to the first inner handle side 116 or the second inner handle side 118. The liner lock can spring out laterally from the inner handle side when the blade 102 is at least partially deployed from the blade cavity 300 and a tip or end of the liner lock can contact or jam against the tang 106 of the blade 102 to lock the blade 102 into place when the folding knife 100 is in the open configuration 204.

Figure 4:
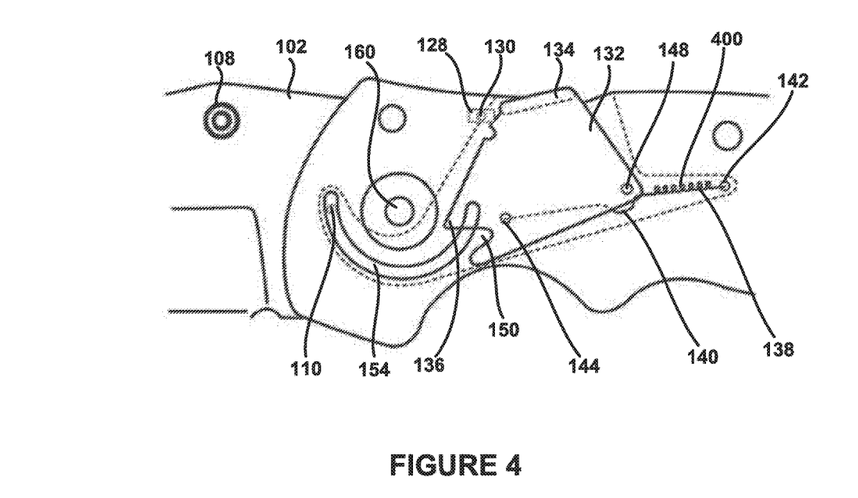
FIG. 4 illustrates a close-up side view of the assisted-open mechanism of the folding knife of FIG. 1 in an assembled state and open configuration.

FIG. 4 illustrates a close-up side view of the assisted-open mechanism of the folding knife 100 of FIG. 1 in an assembled state. The assisted-open mechanism can comprise, but is not limited to, the toggle component 132, the spring 138, the pivot pin 148, the drive pin 110, the clearance slot 154, the locking slide bar 128, and the locking slide pin 130.

FIG. 4 also illustrates that the spring 138 can have at least one coiled segment 400, the arcuate segment 140, and one or more straight segments. The spring 138 can be coupled to the toggle component 132 at the toggle site 144. The spring 138 can be coupled to the toggle site 144 at one end of the spring 138. The spring 138 can also be coupled to the first inner handle side 116 at the first inner handle site 142. The spring can be coupled to the first inner handle site 142 at the other end of the spring 138.

Figure 5:
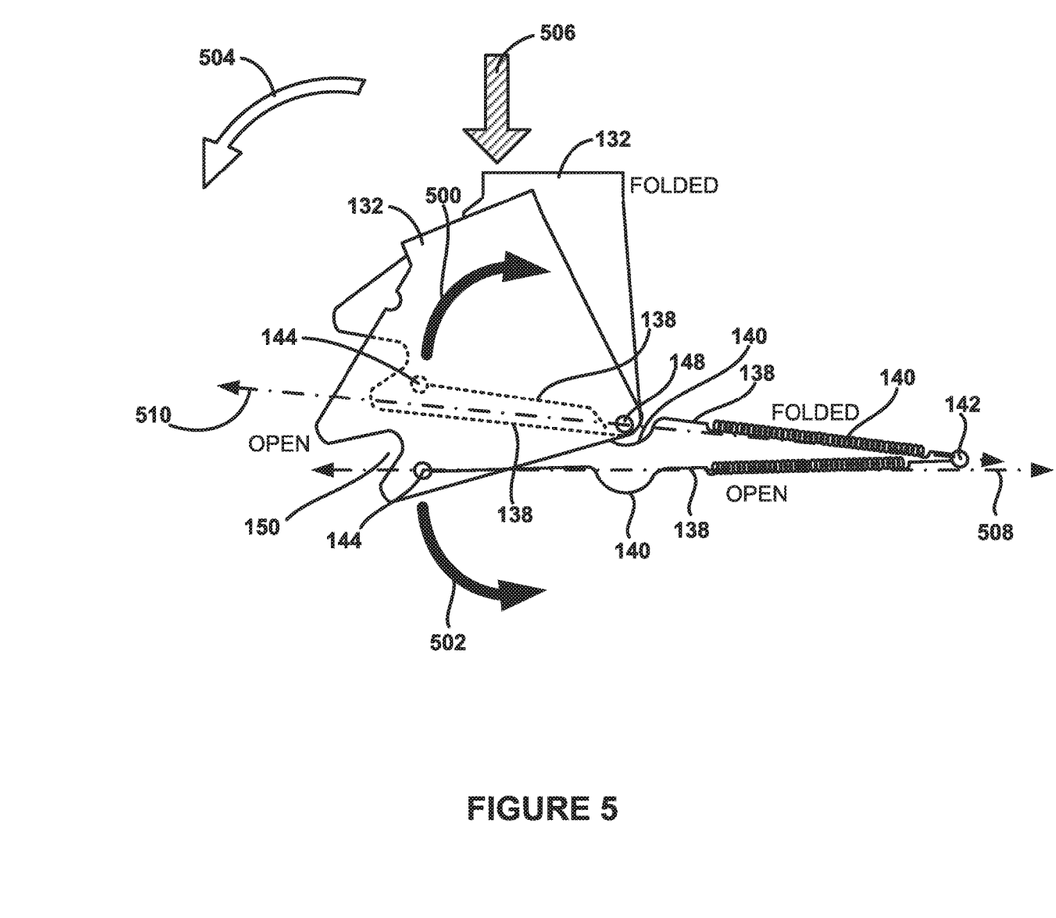
FIG. 5 illustrates a schematic of a toggle component and spring of the assisted-open mechanism in operation.

FIG. 5 illustrates a schematic of the toggle component 132 and the spring 138 of the assisted-open mechanism in operation. The spring 138 can pull the toggle component 132 in a first rotational direction 500 (e.g., a clockwise direction when viewed in the direction of the first inner handle side 116 from the first outer handle side 114) when the folding knife 100 is in the folded configuration 200. As shown in FIG. 5, the spring 138 can have a longitudinal axis 508. The longitudinal axis 508 can be a line running along a length of the spring 138 and used to orient the spring 138. When the spring 138 is connected to the toggle component 132 and the first inner handle side 116, the longitudinal axis 508 can be a line running from the first inner handle site 142 to the toggle site 144. As seen in the figures, the arcuate segment 140 of the spring 138 can be below the longitudinal axis 508 (when viewed in the direction of the first inner handle side 116 from the first outer handle side 114). Also, when the folding knife 100 is in the folded configuration 200, the longitudinal axis 508 can be above the pivot pin 148 when the spring 138 is pulling the toggle component 132 in the first rotational direction 500. The arcuate segment 140 of the spring 138 allows the spring 138 to pull the toggle component 132 in the first rotational direction 500 (e.g., a clockwise direction when viewed in the direction of the first inner handle side 116 from the first outer handle side 114) without the spring 138 being hindered by the pivot pin 148. The arcuate segment 140 of the spring 138 can partially surround or encompass the pivot pin 148 when the spring 138 pulls the toggle component 132 in the first rotational direction 500.

As shown in FIG. 5, the toggle component 132, when pulled by the spring 138, can also have an over-center position 510. The over-center position 510 can be a point along the rotational trajectory of the toggle component 132 where the spring 138 pulls the toggle component 132 in a second rotational direction 502 (e.g., a counterclockwise direction when viewed in the direction of the first inner handle side 116 from the first outer handle side 114) rather than the first rotational direction 500. In one embodiment, the over-center position 510 can be represented by a line extending from the first inner handle site 142 to the pivot pin 148.

The spring 138 can pull the toggle component 132 in the second rotational direction 502 when the longitudinal axis 508 of the spring 138 falls below the over-center position 510 when viewed in the direction of the first inner handle side 116 from the first outer handle side 114. The spring 138 can pull the toggle component 132 in the second rotational direction 502 when the folding knife 100 is in the open configuration 204. In these embodiments, the second rotational direction 502 can be counter to the first rotational direction 500.

The spring 138 can automatically switch from pulling the toggle component 132 in the first rotational direction 500 to pulling the toggle component 132 in the second rotational direction 502 when the toggle component 132 passes the over-center position 510 in response to a force applied to the button top 134 by a user of the folding knife 100 in the direction of the handle bottom 168. For example, the user can apply a force in a downward direction 506 as shown in FIG. 5. Once the toggle component 132 passes the over-center position 510, the force of the spring 138 pulling on the toggle site 144 in the second rotational direction 502 (e.g., counterclockwise) is translated by the toggle nose 136 into a pushing force on the drive pin 110 to rotate the blade 102 in the blade rotational direction 202 (e.g., clockwise).

For example, a user can press or push on the button top 134 of the toggle component 132 to initiate the deployment of the blade 102. In response to a force being applied in the downward direction 506, the toggle component 132 can cause the blade 102 to rotate to approximately 21 degrees from a starting position parallel to the longitudinal axis of the folding knife 100. Once the blade 102 is rotated to 21 degrees, the spring 138 can take over and pull the toggle component 132 in the second rotational direction 502. The pulling of the toggle component 132 in the second rotational direction 502 can cause the blade 102 to rotate to approximately 45 degrees from a starting position parallel to the longitudinal axis of the folding knife 100. Once the blade 102 is rotated to approximately 45 degrees, the user can use the thumb stud 108 or apply a force to the blade 102 to rotate the blade to the open configuration 204.

Figure 6:
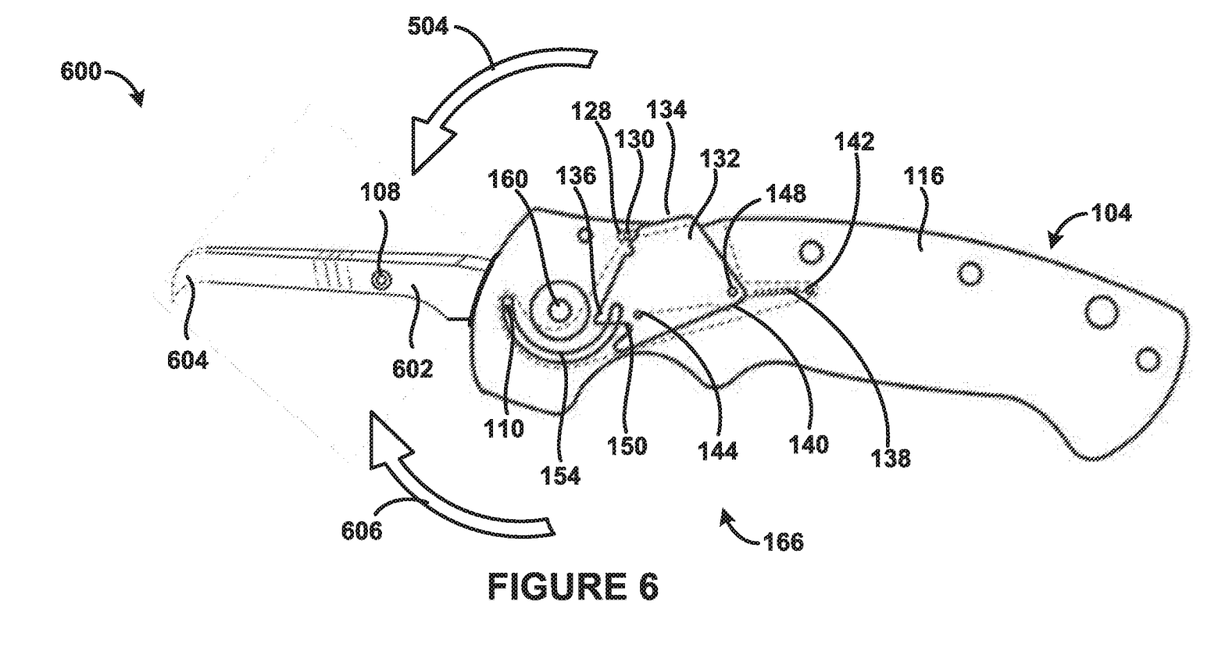
FIG. 6 illustrates an embodiment of a folding utility tool in an open configuration.

FIG. 6 illustrates a folding utility tool 600 in one or more embodiments. The folding utility tool 600 can include a handle 104 comprising a first inner handle side 116 spaced apart from a second inner handle side 118 (see FIGS. 1 and 3). The first inner handle side 116 and the second inner handle side 118 can define a tool cavity in between the two handle sides. A tool arm 602 can be pivotally connected to the handle 104. The tool arm 602 can have a drive pin 110 connected to and extending or projecting out from a side of the tool arm 602. A toggle component 132 can be pivotally connected to at least one of the two handle sides at a pivot pin 148. The toggle component 132 can have a retaining notch 150 defined along an edge of the toggle component 132.

The folding utility tool 600 can include a spring 138 having an arcuate or arc-like segment 140 or a bended segment along a longitudinal axis 508 of the spring 138. The spring 138 can be coupled to at least one of the two handle sides at a first inner handle site 142 at one end of the spring 138 and the toggle component at a toggle site 144 at the other end of the spring 138. The spring 138 can be a tension spring comprising at least one coiled segment 140, the arcuate segment 140, and one or more straight segments. The drive pin 110 of the tool arm 602 can be positioned within the retaining notch 150 when at least part of the tool arm 602 is folded into the tool cavity.

The folding utility tool 600 can also include a clearance slot 154 defined along the first inner handle side 116 (see FIGS. 1, 2A, 2B, 2C, 2D, and 4) and part of the drive pin can project through the clearance slot. The toggle component can also include a button top 134. The toggle component 132 can rotate in a toggle rotational direction 504 (e.g., a counterclockwise direction) in response to a force applied to the button top 134 by a user of the folding utility tool 600 in the direction of the handle bottom 166. The tool arm 602 can be deployed out of the tool cavity in an arm rotational direction 606 (e.g., a clockwise direction) in response to the rotation of the toggle component 132. The toggle rotational direction 504 can be counter to the arm rotational direction 606. The drive pin 110 can move within the clearance slot 154 as the tool arm 602 is rotated. The retaining notch 150 can be defined in part by a toggle nose 136 of the toggle component 132 and the tool arm 602 can be deployed when the toggle nose 136 actuates or biases the drive pin 110 of the tool arm 602 when the toggle component 132 is rotated in the toggle rotational direction 504.

The spring 138 can pull the toggle component 132 in a first rotational direction 500 (e.g., a clockwise direction, see FIG. 5) when the folding utility tool 600 is in a folded configuration 200 (see FIG. 2A). The spring 138 can also pull the toggle component 132 in a second rotational direction 502 (e.g., a counterclockwise direction, see FIG. 5) when the folding utility tool 600 is in an open configuration 204 (see FIG. 2D). In these embodiments, the first rotational direction 500 can be counter to the second rotational direction 502. The spring 138 can pull the toggle component 132 in the second rotational direction 502 when the toggle component 132 passes an over-center position 510 (see FIG. 5) in response to a force applied to the button top 134 by a user of the folding utility tool 600 in the direction of the handle bottom 166. The arcuate segment 140 of the spring 138 can partially surround or encompass the pivot pin 148 when the spring 138 pulls the toggle component 132 in the first rotational direction 500.

The handle 104 can further include at least one outer handle side 114 (see FIG. 1). The toggle component can be positioned in between the outer handle side 114 and the first inner handle side 116.

The folding utility tool 600 can include a tool head 604 coupled to the tool arm 602. The tool head 604 can include a part of a screwdriver, a fork, a spoon, a toothpick, a flossing tool, a corkscrew, a bottle opener, a file, a saw, or a can opener. The tool head 604 can be folded into the tool cavity when the folding utility tool 600 is in the folded configuration 200.

The folding utility tool 600 can further include a locking slide bar 128 coupled to a locking slide pin 130. The locking slide pin 130 can prevent the toggle component 132 from rotating when the locking slide pin 130 contacts and pushes against a locking notch 152 (see FIG. 1) defined along an edge of the toggle component 132.

The folding knife 100 of the present disclosure provides a technological advancement in the safe operation of assisted-open folding knives. For example, the toggle component 132 permits a user to press on the button top 134 of the toggle component 132 to deploy the blade of the folding knife 100. The user is no long required to fumble with the blade 102 or the tang 106 of the blade 102 in order to actuate the assisted-open mechanism.

The folding knife 100 of the present disclosures also provides a more intuitive design for assisted-open folding knives. A user who has never used the folding knife 100 can quickly figure out that the blade 102 of the folding knife 100 can be deployed by pressing down on the button top 134 of the toggle component 132.

A number of embodiments have been described. Nevertheless, it will be understood by one of ordinary skill in the art that various changes and modifications can be made to this disclosure without departing from the spirit and scope of the embodiments. Elements of systems, devices and methods shown with any embodiment are exemplary for the specific embodiment and can be used in combination or otherwise on other embodiments within this disclosure. Accordingly, other embodiments are within the scope of the following claims and the specification and/or drawings may be regarded in an illustrative rather than a restrictive sense.

I claim:

1. A folding knife, comprising:
   a handle comprising at least two handle sides spaced apart and defining a blade cavity therebetween;
   a blade pivotally connected to the handle, wherein the blade comprises a drive pin connected to and extending out from a side of the blade;
   a toggle component pivotally connected to at least one of the at least two handle sides at a pivot pin, wherein the toggle component comprises a retaining notch;
   a spring comprising an arcuate segment along a longitudinal axis of the spring, wherein the spring is coupled to at least one of the at least two handle sides at one end and the toggle component at another end, wherein the drive pin is positioned within the retaining notch when at least part of the blade is folded into the blade cavity; and
   a locking slide bar coupled to a locking slide pin, wherein the locking slide pin prevents the toggle component from rotating when the locking slide pin contacts a locking notch defined along an edge of the toggle component.

2. The folding knife of claim 1, further comprising:
   a clearance slot defined along at least one of the at least two handle sides and at least part of the drive pin projects through the clearance slot; and
   the toggle component further comprises a button top, wherein the toggle component rotates in a toggle rotational direction in response to a force applied to the button top toward a handle bottom and the blade is deployed out of the blade cavity in a blade rotational direction in response to the rotation of the toggle component, and wherein the toggle rotational direction is counter to the blade rotational direction.

3. The folding knife of claim 2, wherein the retaining notch is defined in part by a toggle nose of the toggle component and the blade is deployed when the toggle nose actuates the drive pin of the blade when the toggle component is rotated in the toggle rotational direction.

4. The folding knife of claim 1, wherein the spring pulls the toggle component in a first rotational direction when the folding knife is in a folded configuration and the spring pulls the toggle component in a second rotational direction when the folding knife is in an open configuration, and wherein the first rotational direction is counter to the second rotational direction.

5. The folding knife of claim 4, wherein the spring pulls the toggle component in the second rotational direction when the toggle component passes an over-center position.

6. The folding knife of claim 4, wherein the arcuate segment of the spring partially surrounds the pivot pin when the spring pulls the toggle component in the first rotational direction.

7. The folding knife of claim 1, wherein the spring is a tension spring.

8. The folding knife of claim 1, wherein the handle further comprises at least one outer handle side and the at least two handle sides are inner handle sides and the toggle component is positioned in between the at least one outer handle side and one of the inner handle sides.

9. The folding knife of claim 1, wherein the blade comprises a partial tang and the partial tang rotates in between the at least two handle sides without protruding from a handle top of the handle.

* * * * *